United States Patent
Weadock (12)

(10) Patent No.: US 6,264,596 B1
(45) Date of Patent: *Jul. 24, 2001

(54) IN-SITU RADIOACTIVE MEDICAL DEVICE

(75) Inventor: Kevin S. Weadock, Bound Brook, NJ (US)

(73) Assignee: Meadox Medicals, Inc., Oakland, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/962,749

(22) Filed: Nov. 3, 1997

(51) Int. Cl.$^7$ ................................................ A61N 5/00

(52) U.S. Cl. ................................................ 600/3

(58) Field of Search ............................. 600/1–8

(56) References Cited

U.S. PATENT DOCUMENTS

| | | | |
|---|---|---|---|
| 2,546,761 | 3/1951 | Loftus | 128/1.2 |
| 2,862,108 | 11/1958 | Meilink | 250/106 |
| 2,955,208 | 10/1960 | Stevens | 250/108 |
| 3,060,924 | 10/1962 | Rush | 128/1.2 |
| 3,147,383 | 9/1964 | Prest | 250/108 |

(List continued on next page.)

FOREIGN PATENT DOCUMENTS

| | | |
|---|---|---|
| 2166915 | 8/1996 | (CA) . |
| 9102312 | 8/1992 | (DE) . |
| 195 26 680 A1 | 1/1997 | (DE) . |
| 197 54 870 A1 | 8/1998 | (DE) . |

(List continued on next page.)

OTHER PUBLICATIONS

Sutherland, "Managin Cancer Through Synergy", *Administrative Radiology Journal*, Nov. 1996, pp. 21–27.

Raloff, "Nuclear Medicine Gets Friendlier—Experimental Therapies Seek to Poison Just the Disease", *Science News*, vol. 152, Jul. 19, 1997, pp. 40–41.

Fackelmann, "Harbinger of a Heart Attack—Does a Protein in the Blood Foretell Heart Trouble", *Science News*, vol. 151, Jun. 14, 1997, pp. 374–375.

"Aids and Cancer Cured by Hyper–Oxygenation", *Now What*, Issue No. 1, 1987, Waves Forest, Monterey, California.

Li et al., "Reactive Oxygen Species Induce Apoptosis of Vascular Smooth Muscle Cell", *FEBS Letters*, 404, 1997, pp. 249–252.

Kalli, "Oxygen Emulsion The Question of Free Radicals", Internet Address http://www.livelinks.com/sumeria/oxy/rad2.html, Aug. 1, 1997.

(List continued on next page.)

*Primary Examiner*—John P. Lacyk
(74) *Attorney, Agent, or Firm*—Crompton, Seager & Tufte, LLC.

(57) ABSTRACT

Devices and methods for rendering an intravascular stent radioactive in-situ, after stent placement. A stent is provided having a tubular body and a first substance immobilized on body. The first substance preferably has a high and selective affinity for a second substance which can be radioactive, cytotoxic or thrombolytic. The first substance can also have an affinity for growth factors or thrombolytic, chemolytic or cytotoxic agents. The stent can be placed across a stenosed blood vessel region, preferably after dilation by angioplasty or atherectomy. After stent placement within the vessel, the second substance can be injected into the blood stream of a patient. With each pass through the stent, the second substance is increasingly bound to the first substance on the stent. Suitable complementary substance pairs include avidin and radio-labeled biotin, protamine and radioactive heparin, and protein and anti-protein antibody.

47 Claims, 1 Drawing Sheet

U.S. PATENT DOCUMENTS

| | | | |
|---|---|---|---|
| 3,324,847 | 6/1967 | Zoumboulis | 128/1.2 |
| 3,505,991 | 4/1970 | Hellerstein et al. | 128/1.1 |
| 3,643,096 | 2/1972 | Jeffries, Jr. et al. | 250/108 R |
| 3,669,093 | 6/1972 | Sauerwein et al. | 128/1.1 |
| 3,674,006 | 7/1972 | Holmer | 128/1.2 |
| 3,750,653 | 8/1973 | Simon | 128/1.2 |
| 3,811,426 | 5/1974 | Culver et al. | 128/1.2 |
| 3,861,380 | 1/1975 | Chassagne et al. | 128/1.2 |
| 3,866,050 | 2/1975 | Whitfield | 250/497 |
| 3,927,325 | 12/1975 | Hungate et al. | 250/435 |
| 4,096,862 | 6/1978 | DeLuca | 128/348 |
| 4,220,864 | 9/1980 | Sauerwein et al. | 250/497 |
| 4,225,790 | 9/1980 | Parsons, Jr. et al. | 250/497 |
| 4,244,357 | 1/1981 | Morrison | 128/1.2 |
| 4,281,252 | 7/1981 | Parsons, Jr. et al. | 250/497 |
| 4,314,157 | 2/1982 | Gaines | 250/497 |
| 4,364,376 | 12/1982 | Bigham | 128/1.1 |
| 4,584,991 | 4/1986 | Tokita et al. | 128/1.1 |
| 4,588,395 | 5/1986 | Lemelson | 604/59 |
| 4,631,415 | 12/1986 | Sauerwein et al. | 250/497.1 |
| 4,702,228 | 10/1987 | Russell, Jr. et al. | 128/1.2 |
| 4,706,652 | 11/1987 | Horowitz | 128/1.2 |
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russell, Jr. et al. | 128/1.2 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala et al. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,976,690 | 12/1990 | Solar et al. | 604/96 |
| 5,030,194 | 7/1991 | Van't Hooft | 600/3 |
| 5,032,113 | 7/1991 | Burns | 604/96 |
| 5,057,313 | 10/1991 | Shih et al. | 424/85.91 |
| 5,059,166 | 10/1991 | Fischell et al. | 600/3 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 * | 1/1993 | Fischell et al. | 600/3 |
| 5,183,455 | 2/1993 | Hayman et al. | 600/7 |
| 5,199,939 | 4/1993 | Dake et al. | 600/3 |
| 5,213,561 | 5/1993 | Weinstein et al. | 600/7 |
| 5,267,960 | 12/1993 | Hayman et al. | 604/106 |
| 5,282,781 | 2/1994 | Liprie | 600/3 |
| 5,302,168 * | 4/1994 | Hess | 600/3 |
| 5,308,356 | 5/1994 | Blackshear, Jr. et al. | 606/194 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,391,139 | 2/1995 | Edmundson | 600/7 |
| 5,395,300 | 3/1995 | Liprie | 600/3 |
| 5,405,309 | 4/1995 | Carden, Jr. | 600/3 |
| 5,409,015 | 4/1995 | Palermo | 128/772 |
| 5,411,466 | 5/1995 | Hess | 600/3 |
| 5,425,720 | 6/1995 | Rogalsky et al. | 604/198 |
| 5,429,582 | 7/1995 | Williams | 600/2 |
| 5,482,698 | 1/1996 | Griffiths | 424/141 |
| 5,482,867 | 1/1996 | Barrett et al. | 436/518 |
| 5,482,923 | 1/1996 | Maione | 514/2 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,518,882 | 5/1996 | Lund et al. | 435/6 |
| 5,532,122 | 7/1996 | Drukier | 435/5 |
| 5,538,494 | 7/1996 | Matsuda | 600/1 |
| 5,540,659 | 7/1996 | Teirstein | 604/104 |
| 5,545,132 | 8/1996 | Fagan et al. | 604/96 |
| 5,556,389 | 9/1996 | Liprie | 604/264 |
| 5,556,982 | 9/1996 | Fritzberg et al. | 548/303.7 |
| 5,575,749 | 11/1996 | Liprie | 600/3 |
| 5,580,962 | 12/1996 | Eibl et al. | 530/395 |
| 5,588,962 | 12/1996 | Nicholas et al. | 604/52 |
| 5,605,530 | 2/1997 | Fischell et al. | 600/3 |
| 5,607,659 | 3/1997 | Gustavson et al. | 424/1.73 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,637,759 | 6/1997 | Hearst et al. | 560/159 |
| 5,639,727 | 6/1997 | Little, II | 514/12 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,713,828 | 2/1998 | Coniglione | 600/7 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,833,593 | 11/1998 | Liprie | 600/3 |
| 5,840,008 | 11/1998 | Klein et al. | 600/3 |
| 5,840,009 | 11/1998 | Fischell et al. | 600/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 | 1/1999 | Hastings et al. | 600/3 |
| 5,857,956 | 1/1999 | Liprie | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 * | 2/1999 | Eury | 600/3 |
| 5,871,437 * | 2/1999 | Alt | 600/3 |
| 5,873,811 * | 2/1999 | Wang et al. | 600/3 |
| 5,879,282 | 3/1999 | Fischell et al. | 600/3 |
| 5,882,290 | 3/1999 | Kume | 600/3 |
| 5,882,291 | 3/1999 | Bradshaw et al. | 600/3 |
| 5,891,091 | 4/1999 | Teirstein | 604/104 |
| 5,897,573 | 4/1999 | Rosenthal et al. | 606/224 |
| 5,899,882 | 5/1999 | Waksman et al. | 604/96 |
| 5,906,573 | 5/1999 | Aretz | 600/3 |
| 5,910,101 | 6/1999 | Andrews et al. | 600/3 |
| 5,910,102 | 6/1999 | Hastings | 600/3 |

| | | | | | | |
|---|---|---|---|---|---|---|
| 5,913,813 | 6/1999 | Williams et al. | 600/3 | WO 97/17029 | 5/1997 | (WO) . |
| 5,916,143 | 6/1999 | Apple et al. | 600/3 | WO 97/18012 | 5/1997 | (WO) . |
| 5,919,126 | 7/1999 | Armini | 600/3 | WO 97/19706 | 6/1997 | (WO) . |
| 5,924,973 | 7/1999 | Weinberger | 600/3 | WO 97/25102 | 7/1997 | (WO) . |
| 5,924,974 | 7/1999 | Loffler | 600/3 | WO 97/25103 | 7/1997 | (WO) . |
| 5,938,582 | 8/1999 | Ciamacco, Jr. et al. | 600/3 | WO 97/40889 | 11/1997 | (WO) . |
| 5,947,889 | 9/1999 | Hehrlein | 600/3 | WO 98/01183 | 1/1998 | (WO) . |
| 5,947,924 | 9/1999 | Liprie | 604/96 | WO 98/01184 | 1/1998 | (WO) . |
| 5,947,958 | 9/1999 | Woodard et al. | 606/1.5 | WO 98/01185 | 1/1998 | (WO) . |
| 5,957,829 | 9/1999 | Thornton | 600/3 | WO 98/01186 | 1/1998 | (WO) . |
| 5,961,439 | 10/1999 | Chernomorsky et al. | 600/4 | WO 98/11936 | 3/1998 | (WO) . |
| 5,967,966 | 10/1999 | Kronholz et al. | 600/3 | WO 98/16151 | 4/1998 | (WO) . |
| 5,971,909 | 10/1999 | Bradshaw et al. | 600/3 | WO 98/20935 | 5/1998 | (WO) . |
| 5,976,106 | 11/1999 | Verin et al. | 604/96 | WO 98/25674 | 6/1998 | (WO) . |
| 5,997,462 | 12/1999 | Loffler | 600/3 | WO 98/29049 | 7/1998 | (WO) . |
| 5,997,463 | 12/1999 | Cutrer | 600/8 | WO 98/30273 | 7/1998 | (WO) . |
| 6,010,445 | 1/2000 | Armini et al. | 600/3 | WO 98/34681 | 8/1998 | (WO) . |
| 6,013,019 | 1/2000 | Fischell et al. | 600/3 | WO 98/36788 | 8/1998 | (WO) . |
| 6,013,020 | 1/2000 | Meloul et al. | 600/7 | WO 98/36790 | 8/1998 | (WO) . |
| 6,024,690 | 2/2000 | Lee et al. | 600/3 | WO 98/36796 | 8/1998 | (WO) . |
| 6,030,333 | 2/2000 | Sioshansi et al. | 600/3 | WO 98/39052 | 9/1998 | (WO) . |
| 6,033,357 | 3/2000 | Ciezki et al. | 600/3 | WO 98/39062 | 9/1998 | (WO) . |

FOREIGN PATENT DOCUMENTS

| | | | | | |
|---|---|---|---|---|---|
| 197 24 233 C1 | 12/1998 | (DE) . | WO 98/39063 | 9/1998 | (WO) . |
| 197 58 234 | 7/1999 | (DE) . | WO 98/40032 | 9/1998 | (WO) . |
| 198 07 727 | 7/1999 | (DE) . | WO 98/46309 | 10/1998 | (WO) . |
| 198 25 563 | 12/1999 | (DE) . | WO 98/55179 | 12/1998 | (WO) . |
| 198 25 999 | 12/1999 | (DE) . | WO 98/57706 | 12/1998 | (WO) . |
| 198 26 000 | 12/1999 | (DE) . | WO 99/01179 | 1/1999 | (WO) . |
| 198 29 447 | 1/2000 | (DE) . | WO 99/02219 | 1/1999 | (WO) . |
| 0 497 495 A2 | 8/1992 | (EP) . | WO 99/04706 | 2/1999 | (WO) . |
| 0 514 913 A2 | 11/1992 | (EP) . | WO 99/04856 | 2/1999 | (WO) . |
| 0 593 136 A1 | 4/1994 | (EP) . | WO 99/10045 | 3/1999 | (WO) . |
| 0 433 011 B1 | 7/1994 | (EP) . | WO 99/21615 | 5/1999 | (WO) . |
| 0 633 041 A1 | 1/1995 | (EP) . | WO 99/21616 | 5/1999 | (WO) . |
| 0 686 342 A1 | 12/1995 | (EP) . | WO 99/22774 | 5/1999 | (WO) . |
| 0 688 580 A1 | 12/1995 | (EP) . | WO 99/22775 | 5/1999 | (WO) . |
| 0 696 906 B1 | 2/1996 | (EP) . | WO 99/22812 | 5/1999 | (WO) . |
| 0 749 764 A1 | 12/1996 | (EP) . | WO 99/22815 | 5/1999 | (WO) . |
| 0 754 472 A2 | 1/1997 | (EP) . | WO 99/24116 | 5/1999 | (WO) . |
| 0 754 473 A2 | 1/1997 | (EP) . | WO 99/24117 | 5/1999 | (WO) . |
| 0 778 051 A1 | 6/1997 | (EP) . | WO 99/29354 | 6/1999 | (WO) . |
| 0 801 961 A2 | 10/1997 | (EP) . | WO 99/29370 | 6/1999 | (WO) . |
| 0 810 004 | 12/1997 | (EP) . | WO 99/29371 | 6/1999 | (WO) . |
| 0 813 894 A2 | 12/1997 | (EP) . | WO 99/30779 | 6/1999 | (WO) . |
| 0 629 380 B1 | 7/1998 | (EP) . | WO 99/34969 | 7/1999 | (WO) . |
| 0 865 803 | 9/1998 | (EP) . | WO 99/36121 | 7/1999 | (WO) . |
| 0 904 798 | 3/1999 | (EP) . | WO 99/39628 | 8/1999 | (WO) . |
| 0 904 799 | 3/1999 | (EP) . | WO 99/40962 | 8/1999 | (WO) . |
| 10071210 | 3/1998 | (JP) . | WO 99/40970 | 8/1999 | (WO) . |
| WO 86/03124 | 6/1986 | (WO) . | WO 99/40971 | 8/1999 | (WO) . |
| WO 93/04735 | 3/1993 | (WO) . | WO 99/40972 | 8/1999 | (WO) . |
| WO 94/25106 | 11/1994 | (WO) . | WO 99/40973 | 8/1999 | (WO) . |
| WO 94/26205 | 11/1994 | (WO) . | WO 99/40974 | 8/1999 | (WO) . |
| WO 95/07732 | 3/1995 | (WO) . | WO 99/42162 | 8/1999 | (WO) . |
| WO 95/19807 | 7/1995 | (WO) . | WO 99/42163 | 8/1999 | (WO) . |
| WO 95/26681 | 10/1995 | (WO) . | WO 99/42177 | 8/1999 | (WO) . |
| WO 96/06654 | 3/1996 | (WO) . | WO 99/44686 | 9/1999 | (WO) . |
| WO 96/10436 | 4/1996 | (WO) . | WO 99/44687 | 9/1999 | (WO) . |
| WO 96/13303 | 5/1996 | (WO) . | WO 99/49935 | 10/1999 | (WO) . |
| WO 96/14898 | 5/1996 | (WO) . | WO 99/56825 | 11/1999 | (WO) . |
| WO 96/17654 | 6/1996 | (WO) . | WO 99/56828 | 11/1999 | (WO) . |
| WO 96/22121 | 7/1996 | (WO) . | WO 99/61107 | 12/1999 | (WO) . |
| WO 96/29943 | 10/1996 | (WO) . | WO 99/62598 | 12/1999 | (WO) . |
| WO 96/40352 | 12/1996 | (WO) . | WO 99/66979 | 12/1999 | (WO) . |
| WO 97/07740 | 3/1997 | (WO) . | WO 00/03292 | 1/2000 | (WO) . |
| WO 97/09937 | 3/1997 | (WO) . | WO 00/04838 | 2/2000 | (WO) . |
| | | | WO 00/04953 | 2/2000 | (WO) . |
| | | | WO 00/09212 | 2/2000 | (WO) . |

OTHER PUBLICATIONS

Barry, "Reactive Oxygen Species in Living Systems—Source: Biochemistry, and the Role in Human Disease", Internet Address http://www.livelinks.com/sumeria/oxy/reactive.html, Jul. 21, 1997 from *Amercian Journal of Medicine*, vol. 91, No. 3C, Sep. 30, 1991, p. 14S(9).

Block, "Peroxygen Compounds, Chapter 9", *Disinfection, Sterilization, and Preservation*, Fourth Edition, Lea & Febiger, Philadelphia, Copyright 1991.

Moore, "Free Radial Generation by Thyroid Peroxidase and Its Effects on Cells in Vitro", PhD. Dissertation, Group in Endocrinology–University of California, Berkeley, California, Dec. 1990.

Tjho–Heslinga et al., "Results of Ruthenium Irradiation of Uveal Melanoma", *Radiotherapty and Oncology*, vol. 29, 1993, pp. 33–38.

Lommatzsch et al., "Radiation Effects on the Optic Nerve Observed After Brachytherapy of Choroidal Melanomas with 106Ru/106Rh Plaques", *Graefe's Arch. Clin. Expo. Ophthalmol.*, 1994, 232:482–487.

Alberti, *Radiotherapy of Intraocular and Orbital Tumors*, Springer–Verlag, Berlin, Copyright 1993, pp. 363–367 and 23–30.

* cited by examiner

IN-SITU RADIOACTIVE MEDICAL DEVICE

FIELD OF THE INVENTION

The present invention is related to intra-vascular stents. More specifically, the present invention is related to a non-radioactive stent capable of being made radioactive in-situ, after placement within a blood vessel. The stent can be used to inhibit restenosis of blood vessels.

BACKGROUND OF THE INVENTION

Coronary arteries provide blood and nutrients to the heart muscle. The arteries are subject to atherosclerosis or hardening of the arteries. Vascular regions have plaques formed within, resulting in stenosed regions having reduced cross-sectional area. The reduced area causes a reduction in transport of blood, oxygen, and nutrients which can result in angina, myocardial infarction and death.

A commonly used method for treating atherosclerosis is Percutaneous Transluminal Coronary Angioplasty (PTCA). PTCA includes insertion of a balloon catheter through an incision in the femoral artery near the groin, advancement of the balloon over the aortic arch, further advancement within the selected coronary artery, continuing until the balloon portion is placed across the stenosed region. The balloon is inflated, widening the narrowed vessel region.

After catheter withdrawal, significant vessel reclosure may develop. The reclosure may occur within hours or days of dilation, an "abrupt reclosure." When reclosure does occur, however, it more commonly occurs progressively, within six months of the angioplasty. The gradual reclosure is referred to as "restenosis", and largely negates the dilatation treatment. More highly stenosed vessel regions have a greater chance of becoming restenosed.

One approach to dealing with restenosis utilizes stents which are short tubular sections having a lumen therethrough, placed across the recently dilated vessel region. Stents can be either self-expanding or balloon-expandable. Stents are normally left in place indefinitely.

Use of radiation to kill and inhibit growth of cancerous cells is well known. The use of radiation to inhibit restenosis has been proposed. Use of a catheter having a radioactive source on the distal end has been proposed in U.S. Pat. No. 5,199,939 (Dake et al.). The catheter must be held in place during the entire therapy, which is considerably shorter than the months long period over which restenosis is believed to occur. Any radiation delivered must be delivered within the short period the catheter tip is in place. U.S. Pat. No. 5,059,166 (Fischell et al.) proposes using a radioactive stent. As a stent can be left in place indefinitely, the radiation exposure period more closely matches the time period over which restenosis can occur.

Use of a radioactive stent can present drawbacks. A radioactive stent can require shielding both during storage and during placement within the patient. During stent placement, the stent is normally mounted within a delivery device and inserted into the vasculature of the patient. A common entry site is an incision in the femoral artery near the groin. The stent placement procedure is typically performed with several medical personnel present who require shielding if the radiation source is sufficiently strong.

Radioactive stents can have a shelf-life limitation, especially when the radioisotope has a half-life on the same order as the expected shelf life. For example, a stent made radioactive with an isotope having a half-life of about a month will lose half its radioactivity in a month on the shelf. This can present a variation in radiation strength dependent upon the time a stent resides in a warehouse or sits unused in a hospital. The half-life of a radioisotope, if sufficiently small, can preclude its use with stent technology if a significant portion of radioactivity is lost during stent manufacture, shipping and storage. Another limitation with current stent technology is that the stent radioactivity must be decided at the time of manufacture rather than treatment.

What remains to be provided is a method for delivering concentrated radiation at a dilated, stented site without requiring placement of a radioactive stent. What remains to be provided is a device allowing placement of a non-radioactive stent within the vasculature which can be made radioactive in-situ, after placement.

SUMMARY OF THE INVENTION

The present invention includes devices and methods for inhibiting restenosis of blood vessels using stents. The stents are non-radioactive when placed within the blood vessel and are made radioactive in-situ, after placement within the vessel. Stents according to the present invention are adapted to bind a radioactive substance which is preferably injected into the blood stream after stent placement. The stent preferably has a strong and selective affinity for binding the radioactive substance. A preferred stent attains the binding affinity by having a first substance immobilized on the stent surface, where the first substance is adapted to bind the later-to-be injected radioactive substance. The injected radioactive substance is bound to, and is collected at, the stent, thereby concentrating radiation over the stent.

A preferred stent is tubular in shape and has a stent body, with the first substance immobilized on the stent body. In one embodiment, the first substance is avidin and the second substance is radioactive or radio-labeled biotin. In another embodiment, the first substance is protamine and the second substance is radio-labeled heparin. Protamines are strongly basic proteins of relatively low molecular weight. Heparin is an acid mucopolysaccharide. Protamine and heparin also exhibit a highly selective affinity for each other. Other complementary pairs within the scope of the invention include proteins/antibodies, ligands/anti-ligands, and proteins/monoclonal antibodies.

In use, the stent, either self-expanding or expandable, can be put into place using well known devices such as pusher tubes or stent delivery balloon catheters. Stents are preferably put into position after a stenosis dilation procedure such as angioplasty or atherectomy. A preferred use of the stents is the inhibition of restenosis in coronary arteries after angioplasty. After the stent expands into position across a stenosed vessel region, the stent delivery equipment can be removed from the patient. If desired, the patient can be removed from the site of the dilation procedure.

The second, radioactive substance can then be provided, preferably in shielded form. In one method, a shielded hypodermic syringe is provided. In another method, the radioactive substance is injected into an I.V. bag. The radioactive substance can be injected into the blood stream of the patient using any suitable injection means and body site. The radiation exposure can thus be limited to a short time period and a small, easily shielded area. The number of people exposed to the radiation and possibly requiring shielding can be much more limited during an injection than during a stent placement procedure in an operating room. In particular, only radiation medicine personnel need be present during injection.

After injection, the radioactive substance circulates through the blood stream of the patient, with a portion passing through a stented site such as a coronary artery. With each pass through the stent, a substantial amount of the radioactive substance is bound to the stent. Over time, a substantial portion of the radioactive substance is selectively bound to the stent, thereby rendering the stent radioactive and providing radiation to the vessel and inhibiting restenosis. The remainder of the radioactive substance is processed by the liver and excreted in urine. The present invention can be provided as a stent suitable for later injection of a complementary radioactive substance, or as a kit having both stent and complementary radioactive substance.

In one method, radioactive substance is injected one time after stent implantation. The amount of radiation to be delivered can be decided at the time of injection. In another method, radioactive substance can be injected multiple times, over a longer time period. Thus, both the amount of radioactive dosage and the number of doses can be tailored to a particular treatment situation.

DETAILED DESCRIPTION OF THE PREFERRED EMBODIMENTS

Figure 1:
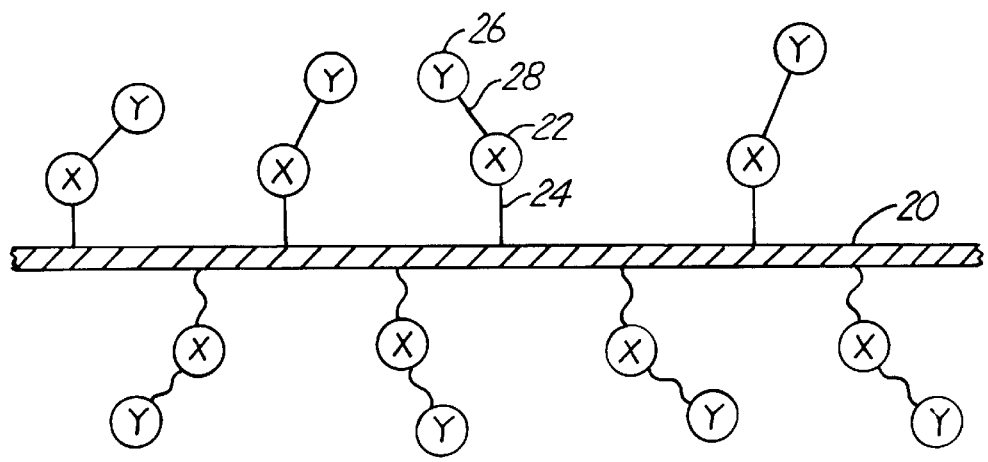
FIG. 1 is a highly diagrammatic view of a stent surface having a ligand immobilized thereon and a radioactive anti-ligand bound to the ligand.

FIG. 1 illustrates in highly diagrammatic form, a stent surface 20 having a first substance or ligand 22 immobilized thereon. Ligand 22 is labelled "X" in FIG. 1. Ligand 22 is immobilized with a bond 24. A second substance or anti-ligand 26 is bound to ligand 22 with a bond 28. Second substance or moiety 26 is radioactive. Anti-ligand 26 is labelled "Y" in FIG. 1. As used herein, ligand/anti-ligand pairs demonstrate specific binding, preferably of relatively high affinity.

Stents preferably have a tubular form. One stent according to the present invention is formed of Nitinol. Another stent is formed of stainless steel. Yet another stent is polymeric. Some tubular stents are formed of wires woven into braids or wound into helixes. Other stents are formed of substantially solid material. Both self expanding and balloon expandable stents are suitable for use with the current invention.

One complementary binding pair of substances suitable for use with the present invention is the avidin/biotin pair. The avidin-biotin complementary pair is commonly used in affinity column chromatography. Avidin is a protein having four identical sub-units, each having a molecular weight of about 70,000. Biotin is a molecule which acts as the prosthetic group in a number of enzymes. Avidin and biotin exhibit a strong and highly selective affinity for each other, having a dissociation constant of about $10^{-15}$ M. The avidin-biotin binding is essentially irreversible. In this pair, avidin or streptavidin can be the ligand and biotin the anti-ligand and can be radio-labeled with isotopes such as $I^{131}$ or $Y^{90}$. In one embodiment, biotin is the ligand and radio-labeled avidin or streptavidin the anti-ligand. Biotin and methods of biotinylation are known. See for example, Hoffman et al. (1977) Proc. Natl. Acad. Sci. USA 74:2697–2700 or Berman and Basch, (1980) "Amplification of the biotin-avidin immunofluorescence technique", J. Immunol. Meth. 36:335–338, both of which are herein incorporated by reference. Biotin can be immobilized on a metallic stent by chelating agents which have affinity for metals, silanes, or other forms of molecular grafting known by those skilled in the art. Biotin can be immobilized upon a polymeric stent by using crosslinking agents or the above-mentioned metallic stent agents.

Another complementary pair of substances suitable for practicing the present invention is the protamine/heparin pair. Heparin is commonly used in open heart surgery to prevent clotting during the procedure. Protamine is injected into a patient after completion of surgery to bind tightly to the heparin and render it ineffective as an anti-coagulant. In practicing the present invention, protamine is the ligand and radio-labeled heparin is the anti-ligand. Non-radioactive heparin can also be used to prevent clotting on the stent. Protamine can be immobilized on a metallic stent through use of chelating agents having an affinity for the metal and protamine or through plasma deposition.

Other ligand/anti-ligand pairs believed suitable for use with the current invention include zinc finger protein/dsDNA fragment, hapten/antibody, lectin/carbohydrate, chelate/binding pair member, and ligand/receptor. Complementary pairs used in the present invention preferably exhibit very selective binding and have a very low dissociation constant. Preferably, the dissociation constant is less than about $10^{-12}$ M, more preferably less than about $10^{-14}$ M, most preferably less than about $10^{-15}$ M.

Radioisotopes that can be bound to the anti-ligand include $I^{131}$, $Y^{90}$, $n^{111}$, and $p^{32}$. A preferred radioisotope is $I^{131}$. Alpha emitting radioisotopes are less preferred than Beta and Gamma emitters, but are within the scope of the invention. The radioisotope can be affixed to the anti-ligand by methods such as iodination via a chloramine-T based system. As used herein, the term "radioactive substance" refers to both a substance having radioactive atoms incorporated therein and to a substance radio-labeled with an additional or substituted radioactive atom not normally found in the native substance.

Other, not necessarily radioactive substances can be bound to the anti-ligand. In one embodiment, cytotoxic or chemolytic substances are bound to the anti-ligand for the purpose of inhibiting restensosis. In another embodiment, growth factors are bound to the anti-ligand. In yet another embodiment, a thrombolytic agent, such as non-radioactive heparin, is bound to the anti-ligand. Thrombolytic agents can dissolve thrombus formed on the stent surface. In still another embodiment, anti-thrombogenic agents are bound to the anti-ligand. Anti-thrombogenic agents can inhibit formation of thrombus on the stent surface. These other substances can be delivered either alone or in conjunction with radioactive substances.

In use, a stent can be prepared by immobilizing a first substance or ligand on the surface using a method as described above. The stent can be mated to a delivery device. Self expanding stents can be compressed within a tubular delivery device while balloon-expandable stents can be mounted upon inflatable balloon catheters. Stent delivery is preferably performed after dilation using a method such as angioplasty or atherectomy. The stent at this point is non-radioactive and requires no special radiation handling or shielding. The stent delivery device can be inserted through the vasculature from an entry point such as an incision in the femoral artery near the groin. The delivery device can be advanced over the aorta and into a coronary artery to a location near the dilated vessel region. The stent can be deployed, either via self-expansion or balloon expansion, until the stent is firmly expanded against the stenosed region walls. The stent delivery device can then be removed.

After stent delivery, in one method, the radioactive anti-ligand or second substance can be immediately prepared and injected into the patient. In a preferred form, the radioactive anti-ligand is prepared in liquid form and enclosed within shielding appropriate for the radiation source. Gamma radiation generally requires heavier shielding than Beta radiation.

The radioactive liquid can be brought to the patient and injected, at any suitable location, into the blood stream of the patient. In one embodiment, the radiation source is shielded during injection, with only an injection needle extending outside the shielding. The injection can be carried out more quickly and easily relative to the more difficult and lengthier procedure of placing a stent. In another embodiment, the radioactive substance is injected into an I.V. bag. In yet another embodiment, the radioactive substance is interposed between an incoming saline line and an outgoing I.V. line to the patient. In this embodiment, the radioactive substance can be contained in a vial such that the vial is flushed by saline. In one method the patient is removed to a different room for injection of the radioactive anti-ligand. In a preferred method, injection of the radioactive anti-ligand takes place within 120 hours of angioplasty or atherectomy. Radioactive injection should take place within this time period as a significant portion of the inhibition of restenosis by radiation is believed to take place within this time period. The radioactive anti-ligand or second substance may also be injected up to several months later.

After injection, the radioactive anti-ligand is circulated through the blood stream, passing the ligand carrying stent. A portion of the radioactive anti-ligand is bound to the ligand sites on the stent with each pass through the coronary arteries of the heart. While only a small portion of blood passes through the coronary arteries with each trip through the heart, that portion is randomly selected and eventually a substantial portion of the radioactive anti-ligand is bound to the stent. The stent has thereby been made radioactive in-situ. Due to tight binding between ligand and anti-ligand, the radioactive substance remains localized at the stent. The now radioactive stent can provide radiation to the stenosed region, thereby inhibiting restenosis.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A medical device adapted for placement at an intravascular treatment site to inhibit restenosis, the device comprising:
    a device surface;
    a first substance immobilized on said device surface; and
    a radioactive second substance suitable for intravascular injection, wherein said first substance is adapted to bind said radioactive second substance when said second substance is intravascularly injected.
2. A medical device as recited in claim 1, wherein said binding is strong and selective between said first and second substance.
3. A medical device as recited in claim 2, wherein said binding has a dissociation constant of less than about $10^{-12}$ M.
4. A medical device as recited in claim 3, wherein said binding has a dissociation constant of less than about $10^{-14}$ M.
5. A medical device as recited in claim 4, wherein said binding has a dissociation constant of less than about $10^{-15}$ M.
6. A medical device as recited in claim 2, wherein said first substance is a ligand and said second substance is an anti-ligand.
7. A medical device as recited in claim 1, wherein said first substance is selected from the group consisting of avidin, streptavidin, and proteins and said second substance is selected from the group consisting of radio-labeled biotin, radio-labeled monoclonal antibodies, and radio-labeled polyclonal antibodies.
8. A medical device as recited in claim 7, wherein said first substance is avidin and said second substance is radio-labeled biotin.
9. A medical device as recited in claim 7, wherein said first substance is protamine and said second substance is radio-labeled heparin.
10. A medical device as recited in claim 7, wherein said first substance is a protein and said second substance is radio-labeled antibody having an affinity for said protein.
11. A medical device as recited in claim 1, wherein said first substance is biotin and said second substance is radio-labeled avidin.
12. A medical device as recited in claim 1, wherein said first substance is biotin and said second substance is radio-labeled streptavidin.
13. A medical device adapted for placement at an intravascular treatment site to inhibit restenosis, the device comprising:
    a device surface;
    a first substance immobilized on said device surface; and
    a radioactive second substance suitable for intravascular injection, wherein said first substance is adapted to bind said radioactive second substance when said second substance is intravascularly injected, said second substance being selectively and strongly bound to said first substance.
14. A medical device as recited in claim 13, wherein said binding is selective and strong between said first and second substance.
15. A medical device as recited in claim 13, wherein said first substance is a ligand and said second substance is an anti-ligand.
16. A medical device as recited in claim 13, wherein said first substance is selected from the group consisting of avidin, streptavidin, and proteins and said second substance is selected from the group consisting of radio-labeled biotin, radio-labeled monoclonal antibodies, and radio-labeled polyclonal antibodies.
17. A medical device as recited in claim 16, wherein said first substance is avidin and said second substance is radio-labeled biotin.
18. A medical device as recited in claim 16, wherein said first substance is biotin and said second substance is selected from the group consisting of radio-labeled avidin and radio-labeled strepavidin.
19. A medical device as recited in claim 16, wherein said first substance is protamine and said second substance is radio-labeled heparin.
20. A medical device as recited in claim 16, wherein said first substance is a protein and said second substance is radio-labeled antibody having an affinity for said protein.
21. A kit for inhibiting restenois in blood vessels comprising:
    a stent including
        a tubular body, and
        a first substance immobilized on said tubular body; and
    a second substance adapted to bind to said first substance when said second substance is intravascularly injected, said second substance being radioactive, said substance being suitable for injection into the human blood stream.

22. A kit as recited in claim 21, wherein said first substance is a ligand and said second substance is an anti-ligand.

23. A kit as recited in claim 21, wherein said first substance is selected from the group consisting of avidin, streptavidin, and proteins and said second substance is selected from the group consisting of radio-labeled biotin, radio-labeled monoclonal antibodies, and radio-labeled polyclonal antibodies.

24. A kit as recited in claim 23, wherein said first substance is avidin and said second substance is radio-labeled biotin.

25. A kit as recited in claim 23, wherein said first substance is biotin and said second substance is selected from the group consisting of radio-labeled avidin and radio-labeled strepavidin.

26. A kit as recited in claim 24, wherein said first substance is protamine and said second substance is radio-labeled heparin.

27. A kit as recited in claim 23, wherein said first substance is a protein and said second substance is radio-labeled antibody having an affinity for said protein.

28. A system for inhibiting restenosis in blood vessels comprising:
a radioactive substance suitable for injection into the human blood stream; and
a stent including
a tubular body, and
means for binding said radioactive substance when said radioactive substance is intravascularly injected, said binding means being immobilized on said tubular body.

29. A method for inhibiting restenosis in a stenosed blood vessel region of a patient comprising the steps:
providing a radioactive substance suitable for injection into the human blood stream;
providing a medical device having a surface and means for binding said radioactive substance, said binding means connected to said surface;
placing said device across said stenosed region;
injecting said radioactive substance into the blood stream, such that said radioactive substance is bound to said binding means.

30. A method for inhibiting restenosis as recited in claim 29, wherein said means for binding includes avidin and said radioactive substance includes radio-labeled biotin.

31. A method for inhibiting restenosis as recited in claim 29, wherein said means for binding includes protamine and said radioactive substance includes radio-labeled heparin.

32. A method for inhibiting restenosis in a stenosed blood vessel region of a patient comprising the steps:
providing a medical device having a surface and a first substance immobilized on said surface;
providing a second substance suitable for injection into the human blood stream, said second substance being radioactive;
placing said medical device at said stenosed region;
injecting said second substance into the blood stream, such that said second substance is substantially bound to said first substance.

33. A method for inhibiting restenosis as recited in claim 32, wherein said first substance includes avidin and said second substance includes radio-labeled biotin.

34. A method for inhibiting restenosis as recited in claim 32, wherein said first substance includes biotin and said second substance is selected from the group consisting of radio-labeled avidin and radio-labeled streptavidin.

35. A method for inhibiting restenosis as recited in claim 32, wherein said first substance includes protamine and said second substance includes radio-labeled heparin.

36. A medical device adapted for intravascular placement comprising:
a device surface;
a first substance immobilized on said surface; and
a second substance suitable for intravascular injection, wherein said first substance is adapted to bind said second substance strongly and selectively when said second substance is intravascularly injected, and wherein said second substance is selected from the group consisting of cytotoxic substances, growth factors, thrombolytic agents and anti-thrombogenic agents.

37. A method for inhibiting restenosis in a stenosed blood vessel region of a patient comprising the steps:
providing a medical device having a surface and a first substance immobilized on said surface;
providing a second substance suitable for injection into the human blood stream, wherein said second substance is selected from the group consisting of cytotoxic substances, growth factors, thrombolytic agents and anti-thrombogenic agents;
placing said medical device at said stenosed region; and
injecting said second substance into said blood stream, such that said second substance is bound to said first substance.

38. A medical device as in claim 1, 13, 21, or 28, wherein the device comprises a tubular body.

39. A medical device as in claim 1, 13, 21, or 28, wherein the device comprises an implantable device.

40. A medical device as in claim 39, wherein the implantable device comprises a stent.

41. A medical device as in claim 1, 13, 21, or 28, wherein the first substance is adapted to bind to a third non-radioactive agent.

42. A medical device as in claim 41, wherein the third agent is a restenosis inhibiting agent.

43. A medical device as in claim 41, wherein the third agent is a growth factor.

44. A medical device as in claim 41, wherein the third agent is a thrombolytic agent.

45. A medical device as in claim 41, wherein the third agent is an anti-thrombogenic agent.

46. A method for inhibiting restenosis as in claim 32, further comprising the steps of:
providing a third substance suitable for injection into the human blood stream, said third substance being non-radioactive and adapted to bind to said first substance;
injecting said third substance into the blood stream such that said third substance is substantially bound to said first substance.

47. A method for inhibiting restenosis as in claim 37, further comprising the steps of:
providing a third substance suitable for injection into the human blood stream, said third substance being radioactive and adapted to bind to said first substance;
injecting said third substance into the blood stream such that said third substance is substantially bound to said first substance.

* * * * *